United States Patent [19]

Gutierrez et al.

[11] 4,344,853
[45] Aug. 17, 1982

[54] FUNCTIONAL FLUID CONTAINING METAL SALTS OF ESTERS OF HYDROCARBYL SUCCINIC ACID OR ANHYDRIDE WITH THIO-BIS-ALKANOLS AS ANTIOXIDANTS

[75] Inventors: Antonio Gutierrez, Mercerville; Stanley J. Brois, Westfield; Jack Ryer, East Brunswick; Harold E. Deen, Cranford, all of N.J.

[73] Assignee: Exxon Research & Engineering Co., Florham Park, N.J.

[21] Appl. No.: 270,137

[22] Filed: Jun. 3, 1981

Related U.S. Application Data

[63] Continuation-in-part of Ser. No. 194,067, Oct. 6, 1980.

[51] Int. Cl.³ .......................... C10M 1/54; C09K 5/00
[52] U.S. Cl. .................................. 252/33.6; 252/48.6; 252/75; 252/400 R
[58] Field of Search ....................... 252/33.6, 48.6, 75, 252/400 R; 260/429.9, 439 CY

[56] References Cited

U.S. PATENT DOCUMENTS

| | | | |
|---|---|---|---|
| 2,540,570 | 2/1951 | Cyphers | 252/46.6 |
| 2,561,232 | 7/1951 | Rudel et al. | 260/485 |
| 3,198,737 | 8/1965 | Calhoun | 252/48.6 |
| 3,278,566 | 10/1966 | Calhoun | 260/400 |
| 3,381,022 | 4/1968 | Le Suer | 252/56 D |
| 3,556,997 | 1/1971 | Leister | 560/195 |
| 3,574,101 | 4/1971 | Murphy | 252/33.6 |
| 3,576,846 | 4/1971 | Leister | 560/195 |
| 3,933,659 | 1/1976 | Lyle et al. | 252/32.7 E |
| 4,105,571 | 8/1978 | Shaub et al. | 252/32.7 E |
| 4,176,074 | 11/1979 | Coupland et al. | 252/32.7 E |

*Primary Examiner*—W. J. Shine
*Attorney, Agent, or Firm*—J. J. Mahon

[57] ABSTRACT

There are disclosed zinc and nickel salts of mono- or di-esters of $C_{12}$–$C_{50}$ aliphatic hydrocarbon substituted succinic acids or anhydrides, such as octadecenyl succinic anhydride, with thio-bis-alkanols such as dithiodiethanol. The products are useful as antioxidants for lubricating oils and functional fluids, especially automatic transmission fluids.

10 Claims, No Drawings

FUNCTIONAL FLUID CONTAINING METAL SALTS OF ESTERS OF HYDROCARBYL SUCCINIC ACID OR ANHYDRIDE WITH THIO-BIS-ALKANOLS AS ANTIOXIDANTS

CROSS-REFERENCE TO RELATED APPLICATIONS

This application is a continuation-in-part of application Ser. No. 194,067 filed Oct. 6, 1980.

The present invention relates to metal salt compounds derived from hydrocarbon substituted succinic acid or anhydride having particular utility as anti-oxidation additives for oleaginous compositions, such as lubricating oils, automatic transmission fluids and similar functional fluids.

More particularly, the invention relates to nickel or zinc salt derivatives of mono- and di-esters of thio-bis-alkanols and alkenyl succinic acids or anhydrides which are especially effective in lubricating oils and automatic transmission fluids (ATF) to provide oxidatively stable compositions.

The prior art contains a wide variety of compounds useful as additives in mineral lubricating oil compositions and in ATF. Representative disclosures are U.S. Pat. No. 3,933,659 issued Jan. 20, 1976 to Lyle et al which reports fatty acid ester and amides as friction modifiers for functional fluids; U.S. Pat. No. 4,176,074 issued Nov. 27, 1979 to Coupland et al describes molybdenum complexes of polyisobutenyl succinic anhydride-amino alkanols as friction modifiers; U.S. Pat. No. 4,105,571 issued Aug. 8, 1978 to Shaub et al discloses glycerol esters of dimerized fatty acids, particularly useful as friction modifiers in lubricating oil compositions.

Diesters of monohydric alcohols, including those with sulfur linkages which have been esterified with $C_3$-$C_{24}$ alkenyl succinic acid are known and are disclosed in U.S. Pat. No. 2,561,232 issued July 17, 1951, to Rudel et al. The diesters disclosed therein are said to be useful as synthetic lubricant fluids. U.S. Pat. Nos. 3,198,737 and 3,278,566 issued to Calhoun, Aug. 3, 1965 and Oct. 11, 1966 disclose fatty esters of thioglycols and other diols useful as intermediates in the preparation of polysulfoxyl esters having utility as extreme pressure agents. U.S. Pat. No. 2,540,570 issued Feb. 6, 1951 to Cyphers discloses glycol esters of rosin or other fatty acids with thioglycols being included in the disclosure, the compounds being useful as extreme pressure additives.

The novel ester compounds themselves and the metal salt derivatives thereof are disclosed and claimed in the aforesaid application Serial No. 194,067 filed Oct. 6, 1980 as novel compositions of matter, the utility being disclosed therein as friction modifiers and corrosion inhibitors. The present invention is based upon the discovery that the nickel and zinc salt derivatives of the novel ester compounds are especially effective as anti-oxidation additives in oleaginous compositions especially automatic transmission fluids and similar mineral oil based functional fluids.

In accordance with the present invention, there are provided hydrocarbon mineral oil functional fluid compositions exhibiting improved oxidative stability containing 0.01 to 1.0 wt. % of an anti-oxidation additive being a zinc or nickel salt of mono- or di-esters, and mixtures thereof, formed by the reaction of (a) thio-bis-alkanols of the formula:

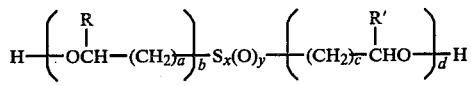

wherein R and R' each independently may be hydrogen, methyl or ethyl, x may be 1-4, y may be 0, 1, or 2; a, b, c, and d each independently may be 1-3 with (b) 1 to 2 moles, per mole of the thio-bis-alkanol, of an aliphatic hydrocarbon substituted succinic acid or anhydride or mixtures thereof wherein the aliphatic hydrocarbon group contains a total of from about 12 to 50 carbon atoms.

As used herein, the term "monoester" or "hemi-ester" refers to product made from equimolar proportions of said thio-bis-alkanol and a succinic acid or anhydride, that is, one free hydroxyl group remains, while the term "di-ester" as used herein refers to those products wherein each hydroxyl group of the thio-bis-alkanol is esterified with a hydrocarbyl substituted or polyolefin substituted succinic acid or anhydride. In either case, a succinic acid moiety remains, i.e. a —C(O)OH group, and this is neutralized with a metal to form zinc or nickel salt derivatives useful as antioxidants in accordance with this invention.

The hydrocarbyl succinic acid or anhydrides are per se known in the art and the commonly used anhydride may be represented by the formula:

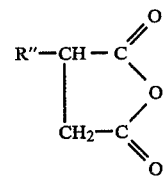

wherein R″ is a $C_{12}$-$C_{50}$ aliphatic hydrocarbon group, such as in alkyl, alkenyl, isoalkyl, isoalkenyl or cycloalkyl hydrocarbyl group. Oligomers containing 12 to 50 carbon atoms are also suitable as the aliphatic hydrocarbyl group such as oligomers of $C_2$-$C_5$ monoolefins such as isobutene.

The aliphatic hydrocarbyl group may be an unsubstituted hydrocarbon group or it may contain substituents such as chlorine, bromine, sulfur, phosphorous or oxygen which will not affect the utility of the final mono- or di-ester product. A preferred substituent is sulfur as exemplified by 2-octadecylthio succinic anhydride.

These compounds may be prepared by the reaction of maleic anhydride with olefins, oligomeric polyolefins, or with chlorinated derivatives thereof using techniques known in the art. Succinic acids are readily produced by hydrolysis of the corresponding anhydride. Especially preferred in preparing the zinc and nickel salts of the mono and di-esters of the present invention are $C_{18}$-$C_{22}$ alkenyl succinic anhydrides, such as octadecenyl succinic anhydride.

The term thio-bis-alkanol as used herein is understood to represent those ester-forming diol compounds of the formula:

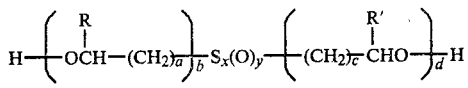

wherein R and R' each independently may be hydrogen, methyl, or ethyl, x may be 1-4, y can be 0, 1 or 2; a, b, c, and d each independently may be 1-3. Thus, if y is 0, the bridging unit is —S—, $S_2$, $S_3$ or $S_4$. When y is 1 or 2, the bridging unit is a sulfinyl or sulfonyl functional group. If b or d are greater than 1, then the formula is meant to express ethoxylated derivatives of such alcohols.

Preferred embodiments are those thio-bis-alkanols within the foregoing formula wherein a, b, c and d are each 1 or 2 any y is 0 with R being H or $CH_3$. Specific compounds include 2,2'-dithiodiethanol 2,2'-thiodiethanol, di(2-hydroxypropyl)disulfide, 3,3'-thiodipropanol and 2,2'-sulfonyldiethanol.

Formation of the mono- and di-esters proceeds by reacting the appropriate quantities of anhydride (or acid) and thio-bis-alkanol with or without an inert organic solvent diluent and heating and stirring the mixture at about 50° to 150° C. until esterification of the anhydride is complete. Equimolar quantities of each reactant will provide mainly the mono- (or hemi-) ester and reaction of 2 moles of hydrocarbon substituted succinic acid or anhydride per mole of thio-bis-alkanol will provide the di-ester material. Also, antioxidative products useful in the present invention encompass zinc and nickel salts of mixtures of such mono- and di-esters.

Insofar as yields are concerned, the reaction of an equimolar ratio of thio-bis-alkanol and hydrocarbon succinic anhydride will provide a product containing about 80% mono-ester and about 20% di-ester. The di-ester is produced in somewhat higher yields, about 90% of the product being di-ester and about 10% monoester when the mole ratio of succinic anhydride to thio-bis-alkanol is 2:1. The metal salts of the di-ester compounds are particularly preferred embodiments for providing the oxidatively stable oleaginous compositions of this invention.

In the case of a di-ester compound, it is suitable to use succinic anhydrides having less than $C_{12}$ hydrocarbon substituent so long as the total number of carbon atoms of the hydrocarbon substituents of the succinic moiety of the ester compounds is at least $C_{12}$ since oil solubility of the finished compound is the important property. Thus, the invention encompasses zinc and nickel salts of symmetrical di-esters based, for example, upon two moles of decenyl succinic anhydride or an asymmetrical di-ester based upon a mole of a $C_3$ hydrocarbon substituted succinic anhydride and a $C_{16}$ hydrocarbon substituted succinic anhydride.

The zinc or nickel metal salts of the mono- and di-esters which are useful as antioxidants in accordance with this invention are salts formed by simply reacting a free succinic acid group of the mono- or di-ester with the metal such as by using zinc or nickel acetate in the presence of xylene and azeotroping acetate acid. It has been found that these should be used such that 0.5 mole of zinc or nickel per mole of monoester or diester is present to provide a suitable antioxidant.

The compositions of this invention include lubricating oils, automatic transmission fluids and similar functional fluids based upon mineral oils such as hydraulic fluids containing the aforesaid metal salts as an oxidation inhibitor. They are employed in typical amounts such as from about 0.01 to 1 weight percent based on the total weight of the composition.

The metal salt antioxidative compounds of the present invention are preferably employed in automatic transmission fluids. Improvements in oxidation stability of ATF has become recently of greater importance because of smaller sump capacities and increased load on a car's cooling system has increased transmission operating temperatures. Such ATF compositions contain a number of conventional additives in amounts providing their normal attendant functions and are typically blended into the mineral oil base in the following ranges:

| Components | Concentration Range (Vol. %) |
|---|---|
| V. I. Improver | 1–15 |
| Corrosion Inhibitor | 0.01–1 |
| Oxidation Inhibitor | 0.01–1 |
| Dispersant | 0.5–10 |
| Pour Point Depressant | 0.01–1 |
| Demulsifier | 0.001–0.1 |
| Anti-Foaming Agents | 0.001–0.1 |
| Anti-Wear Agents | 0.001–1 |
| Seal Swellant | 0.1–5 |
| Friction Modifier | 0.01–1 |
| Mineral Oil Base | Balance |

Typical base oils for automatic transmission fluids include a wide variety of light hydrocarbon mineral oils, such as, naphthenic base, paraffin base and mixtures thereof, having a lubricity viscosity range of about 34 to 45 SUS (Saybolt Universal Seconds) at 38° C.

The invention is further illustrated by the following examples which are not to be considered as limitative of its scope. ATF compositions used in the examples below were formulated in accordance with the components and concentrations noted above and are referred to as Base Fluid; the Base Fluid both with and without the zinc and nickel salts also contained a conventional amine antioxidant.

EXAMPLE 1

This example illustrates the preparation of the di-ester of 2-octadecenyl succinic anhydride and 2,2'-dithio-bis-ethanol which is the precursor of the metal salts prepared in Example 2. About 150 g (0.43 mole) of 2-octadecenyl succinic anhydride was heated to 140° C. while stirring under nitrogen atmosphere. Then 33 g (0.215 mole) of 2,2'-dithio-di-ethanol were added dropwise for a period of ten minutes. The mixture was stirred at this temperature until IR analysis showed the absense of an anhydride carbonyl absorption. Elemental analysis showed 8.1% sulfur; theory for a bis-hemi-ester is 7.5% S.

EXAMPLE 2

This example shows the preparation of the zinc and nickel salts of the di-ester of octadecenyl succinic anhydride and 2,2'dithio-bis-ethanol.

(a) 0.1 mole (85.4 g) of the di-ester of Example 4 was combined with 0.05 mole (10.98 g) of zinc acetate dihydrate in 100 ml. of xylene. The mixture was heated to 140° C. for two hours. The xylene was distilled off and the residue was heated at 150° C. under nitrogen for another hour. The residue solidified when cooled to room temperature. The IR of the solid showed carbonyl absorption bands characteristic of the desired zinc carboxylate salt. Elemental analysis showed 3.72% zinc.

(b) The procedure of (a) above was repeated except that 0.05 mole (10.0 g) nickel acetate in 100 ml. of xylene was used. The residue similarly solidified when cooled to room temperature and the IR spectrum showed absorption bands corresponding to the expected nickel carboxylate salt. Elemental analysis showed 3.59% nickel.

EXAMPLE 3

To a fully formulated automatic transmission fluid (Base Fluid) was added 0.35 wt. % of the zinc salt of Example 2(a) and the nickel salt of Example 2(b). The fluid was evaluated in the LMOT (Laboratory Multiple Oxidation Test) and comparison was made with the same fluid without the zinc and nickel salt.

In this LMOT test 50 ml. of the test fluid containing 2.0 g iron filings plus 5 and copper naphthenate oxidation catalyst is heated to 300° F. and 25 ml. of air per minute is bubbled through the sample. Daily samples are taken and blotter spots of the samples are observed for sludge. The number of days it took for visible sludge to appear is the measured rating of the anti-oxidation effect. A rating of 10–11 days is considered a "pass". The results are given below:

| LMOT RESULTS | |
|---|---|
| Base Fluid | 7 days |
| Base Fluid & Zinc Salt | 15/16 days |
| Base Fluid & Nickel Salt | 11 days |

What is claimed is:

1. A functional fluid composition having oxidative stability comprising a hydrocarbon mineral oil of lubricating viscosity containing as an oxidation inhibitor, about 0.01 to 1 wt. % of a zinc or nickel salt of ester compound formed by the reaction of: (a) a thio-bis-alkanol of the formula:

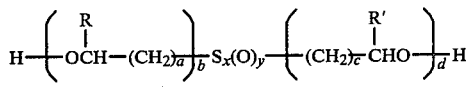

wherein R and R' each independently may be hydrogen, methyl or ethyl, x may be 1–4, y may be 0, 1 or 2 and a, b, c, d each may be independently 1–3, with (b) 1 to 2 moles, per mole of the thio-bis-alkanol, of an aliphatic hydrocarbon substituted succinic acid or anhydride wherein the aliphatic hydrocarbon group contains from about 12 to 50 carbon atoms.

2. A composition according to claim 1 wherein the ester is formed by the reaction of 1 mole of said hydrocarbon succinic acid or anhydride per mole of said thio-bis-alkanol.

3. A composition according to claim 1 wherein the ester is formed by the reaction of 2 moles of said hydrocarbon succinic acid or anhydride per mole of said thio-bis-alkanol.

4. A composition according to claim 1 wherein said ester is a mixture of mono- and di-esters.

5. A composition according to claim 1 wherein said hydrocarbon substituted succinic anhydride is octadecenyl succinic anhydride.

6. A composition according to claim 1 wherein the thio-bis-alkanol is dithiodiethanol of the formula $HOCH_2CH_2S_2CH_2CH_2OH$.

7. The composition of claim 1 wherein the metal is zinc.

8. The composition of claim 1 wherein the metal is nickel.

9. The composition of claim 1 wherein said functional fluid is an automatic transmission fluid.

10. The composition of claim 9 wherein the metal is zinc and said salt contains 0.5 mole of zinc per mole of said ester.

* * * * *